(12) United States Patent
Lucassen et al.

(10) Patent No.: US 8,368,884 B2
(45) Date of Patent: Feb. 5, 2013

(54) SPECTROSCOPIC DETERMINATION OF ANALYTE CONCENTRATION

(75) Inventors: Gerhardus Wilhelmus Lucassen, Eindhoven (NL); Rufus Driessen, Eindhoven (NL); Kristiane Anne Schmidt, Eindhoven (NL); Gerwin Jan Puppels, Rotterdam (NL); Peter Jacobus Caspers, Rotterdam (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 840 days.

(21) Appl. No.: 11/911,557

(22) PCT Filed: Apr. 19, 2006

(86) PCT No.: PCT/IB2006/051210
§ 371 (c)(1),
(2), (4) Date: Jul. 14, 2010

(87) PCT Pub. No.: WO2006/111929
PCT Pub. Date: Oct. 26, 2006

(65) Prior Publication Data
US 2010/0309466 A1    Dec. 9, 2010

(30) Foreign Application Priority Data

Apr. 19, 2005    (EP) ..................................... 05103129

(51) Int. Cl.
*G01J 3/30* (2006.01)
*A61B 5/1455* (2006.01)

(52) U.S. Cl. ........................................................ 356/317

(58) Field of Classification Search .................... 356/39, 356/40, 317–318, 417; 600/317, 319; 250/458.1–461.2; 422/82.07–82.08
See application file for complete search history.

(56) References Cited

U.S. PATENT DOCUMENTS

| 6,240,306 | B1 | 5/2001 | Rohrscheib | |
| 2003/0023151 | A1* | 1/2003 | Khalil et al. | .................. 600/309 |

FOREIGN PATENT DOCUMENTS

| WO | 02057758 A1 | 7/2002 |
| WO | 02057759 A1 | 7/2002 |
| WO | 2004058058 A1 | 7/2004 |
| WO | 2004111621 A1 | 12/2004 |
| WO | 2006090308 A1 | 8/2006 |

* cited by examiner

*Primary Examiner* — Gregory J Toatley
*Assistant Examiner* — Dominic J Bologna

(57) ABSTRACT

A spectroscopic apparatus for determining a concentration and/or spatial gradient of an analyte of a bodily fluid that provides determination of a position of a capillary vessel within a biological sample in order to focus spectroscopic excitation radiation to a volume that is in close proximity to the capillary vessel but does not overlap with the capillary vessel. The provided apparatus exploits the permeability of the vessel wall with respect to an analyte that is subject to analyte concentration determination. By means of biological transport processes, the concentration of an analyte of a bodily fluid located in the capillary vessel influences the concentration in the surrounding of the capillary vessel. Spectroscopic analysis of a volume outside the capillary vessel can therefore serve for a precise and reliable analyte concentration determination inside the capillary vessel.

12 Claims, 6 Drawing Sheets

SPECTROSCOPIC DETERMINATION OF ANALYTE CONCENTRATION

Figure 1:
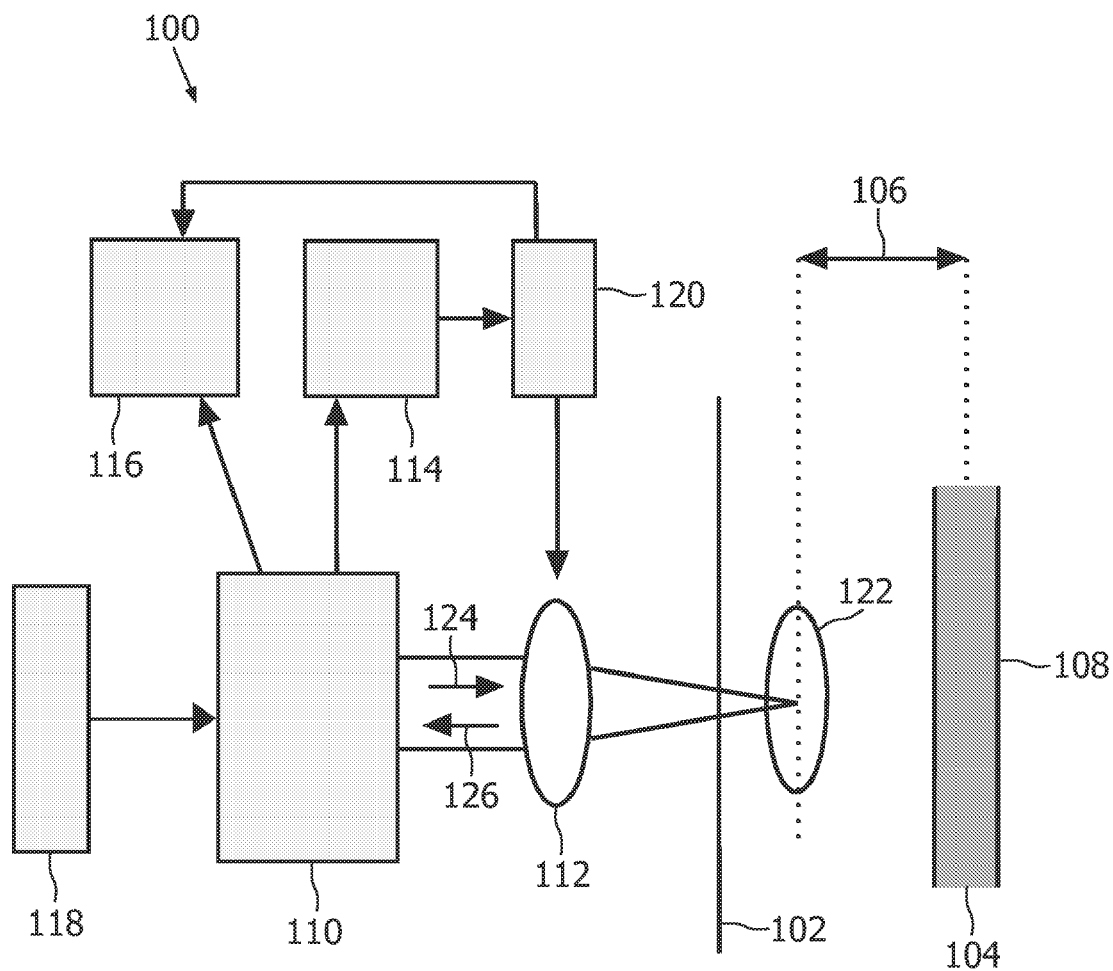

The present invention relates to the field of spectroscopy and more particularly without limitation to non-invasive analyte concentration determination making use of optical imaging and spectroscopic techniques.

Usage of optical spectroscopic techniques for analytical purposes is as such known from the prior art. WO 02/057758 A1 and WO 02/057759 A1 describe spectroscopic analysis apparatuses for in vivo non-invasive spectroscopic analysis of the composition of blood flowing through a capillary vessel of a patient. The position of the capillary vessel is determined by an imaging system in order to identify a region of interest to which an excitation beam for the spectroscopic analysis has to be directed.

The imaging as well as the spectroscopic analysis both make use of a common focusing arrangement enabling imaging of a capillary vessel on the one hand and allowing focusing of a near infrared (NIR) laser beam into the capillary vessel for exciting a Raman spectrum on the other hand. Typically, the focusing arrangement is also used for collection of scattered radiation evolving from the Raman processes.

In vivo non-invasive spectroscopic analysis for determination of a concentration of a distinct analyte of blood is rather sensitive to the composition of the tissue into which the spectroscopic excitation radiation is directed. For instance, focusing an excitation beam into a blood stream or into a blood vessel, the resulting return radiation is severely affected by scattering processes with red blood cells. Furthermore, due to the aspect that there exists many different analytes within the blood, an obtained Raman signal inherently represents spectroscopic information of many constituents of the blood.

Also, the plurality of various Raman signals might become subject to interference, which further complicates the detection of a particular analyte or constituent of a bodily fluid, such as blood. The rather strong dependence of obtained spectroscopic signals on morphology or consistency of spectrally analyzed biological tissue therefore limits the reproducibility of analyte concentration determination.

The present invention therefore aims to provide a spectroscopic apparatus providing improved signal quality and an increased insensitivity towards morphology, structure and composition of investigated tissue.

The present invention provides a spectroscopic apparatus for determining a concentration of an analyte of a bodily fluid, which is inside a capillary vessel. The spectroscopic apparatus comprises an imaging system for determining the position of the capillary vessel, a radiation source for generating spectroscopic excitation radiation and a radiation guiding arrangement for directing excitation radiation into volume in close proximity to the capillary vessel but not overlapping with the capillary vessel. Further, the spectroscopic apparatus comprises a radiation detector for detecting return radiation emanating from the volume in response to excitation radiation irradiation. The apparatus further has a spectroscopic analysis unit providing spectral analysis of return radiation for determining the analyte concentration within the volume and/or within the capillary vessel. Hence, the invention makes effective use of the fact, that the vessel wall of the capillary vessel is at least semipermeable for the analyte whose concentration level has to be determined by means of the spectroscopic apparatus.

It is an advantage of the present invention that for concentration determination of an analyte of a bodily fluid spectroscopic excitation radiation is not directly directed into the bodily fluid or into a stream of the bodily fluid but into a region where only various constituents of the bodily fluid are present but not the fluid in its entirety. For instance, blood plasma leaks out a capillary vessels whereas various components of blood, like red and white blood cells remain inside a volume specified by the capillary vessel walls. The invention effectively exploits the permeability of the capillary vessel wall allowing for a biological transport process to take place resulting e.g. in a diffusion of the analyte of interest into tissue surrounding the capillary vessel.

This allows for a selective analyte concentration determination because only those analytes of the bodily fluid that are capable of penetrating through the capillary vessel wall and that may be subject to a biological transport process can effectively become subject to spectroscopic analysis. As a consequence, those analytes of the bodily fluid that are not capable to penetrate through the vessel wall cannot become subject to spectroscopic investigation according to the present invention.

In contrast non-invasive spectroscopic analysis making use of directly focusing of excitation radiation into a capillary vessel, the inventive procedure effectively prevents that those analytes of the bodily fluid that are not capable to penetrate through the vessel wall do inherently not contribute to the spectroscopic signal that is detectable by means of the detector. Hence, by virtue of the hindered penetration, these analytes no longer have an impact to the spectrum of the return radiation and therefore do no longer affect spectroscopic analyte concentration determination.

Exploiting the aspect that the analyte of interest is capable to penetrate through the vessel wall, the entire spectroscopic procedure does no longer have to be performed inside the capillary vessel itself. Moreover, scattering effects of e.g. red blood cells as well as interference of Raman signals of various constituents of the blood can be reduced to a minimum. This provides an increased signal to noise ratio and improved sensitivity and hence an improved accuracy of the entire spectroscopic analysis.

According to a preferred embodiment, the spectroscopic apparatus further comprises a control unit that is adapted to determine the position of the volume with respect to the determined position of the capillary vessel. Preferably, the control unit is adapted to determine the position of the volume in response to receive an input from the imaging system. The imaging system, which is preferably implemented as an optical image acquisition system, provides position or location information of a capillary vessel that contains the bodily fluid. By means of optical image acquisition and image processing, various parameters specifying an absolute or relative position of the capillary vessel as well as specifying its morphology or geometric structure can be obtained. This information gathered by the imaging system is typically processed by the control unit in order to determine an absolute or relative position as well as a circumference or size of the volume.

The volume determined by means of the control unit typically specifies an inspection volume of the sample, which defines a volume into which excitation radiation is directed into. A portion of the excitation volume from which emanating return radiation is inspected is typically denoted as detection volume and is entirely included in the excitation volume. Hence, the detection volume can completely coincide with the excitation volume but may also specify a smaller volume. In general, the circumference as well as the position of the detection volume can be arbitrarily and independently modified within the circumference of the excitation volume, e.g. by changing a size of a pinhole of a confocal detection arrangement.

Preferably, the control unit autonomously determines position, circumference and structure of the volume in response to parameters obtained from the imaging system or from image processing means. Typically, the position of the volume is determined with respect to the position of the capillary vessel, i.e. the determined position or location of the capillary vessel. For instance, the position of the volume may be specified by a predetermined distance from the capillary vessel not exceeding a predefined threshold. In this way it is effectively guaranteed, that the volume to which spectroscopic excitation radiation is applied, does not overlap with the capillary vessel but is in close proximity to the capillary vessel, such that the concentration of analytes penetrating through the vessel wall does not drop below a minimum detection threshold.

According to a further preferred embodiment of the invention, the radiation guiding arrangement comprises a focusing arrangement for focusing the excitation radiation into the volume. The focusing arrangement additionally provides varying of the focal spot size of the excitation radiation in the volume. In this way either focused or non-focused radiation can be applied to the volume, thus allowing to spectrally investigate a region of variable size. Depending on the analyte of interest and the general properties of the tissue to which the excitation radiation is directed, a larger or smaller focal spot size might be beneficial. Generally, a smaller focal spot size allows for higher radiation intensity in the volume and therefore inherently provides a rather large intensity of the scattered signal. However, focusing the excitation radiation to a rather small spot size, the morphology and internal structure of the tissue surrounding the capillary vessel play a more predominant role. For instance, when applied to bodily tissue, the spectrum of scattered radiation may strongly depend on whether the excitation radiation is focused into the inner part of a cell or to a cell membrane. Consequently, by enlarging the focal spot size of the excitation radiation, aspects of the morphology or internal geometric structure only have a minor impact on the detectable spectroscopic signals. In such a case, the obtained spectrum represents an average of various spectroscopic signals obtained from different biological structures that are located inside the volume. Enlarging of the focal spot size therefore provides an increased insensitivity of the spectroscopic analysis towards the structure of the bodily tissue.

According to a further preferred embodiment of the invention, the volume is moveable with respect to the capillary vessel during the detection of return radiation. For instance, during spectroscopic analysis, i.e. application of excitation radiation into the volume, the volume can be moved, which generally provides dynamic spectroscopic analysis of the vicinity of the capillary vessel. For example, the volume can be moved in such a way that the distance between volume and the capillary vessel varies. In such a configuration, the spectroscopic apparatus provides to determine a spatial concentration gradient of the analyte in the bodily tissue surrounding the capillary vessel. In another constellation, the volume might be moved with respect to the position of the capillary vessel at a constant distance to the capillary vessel.

For instance, if the capillary vessel is an elongated blood vessel, the volume may be moved along the direction of elongation of the capillary vessel. This allows to determine the analyte concentration at numerous locations inside the bodily tissue, each of which having the same distance to the capillary vessel. In this way spatial inhomogeneities of the tissue and/or the capillary vessel or vessel wall can be effectively compensated.

In particular, when moving the volume in such a way that the distance between capillary vessel and the inspection volume changes, the movement should preferably be performed on a timescale which is below the timeframe of diffusion processes inside the bodily tissue. Otherwise temporal fluctuations in the concentration of the analyte may falsify the obtained results. Therefore, an increase of the distance between first and volumes during a spectroscopic analysis shall be performed on a timescale that is smaller than the timescale on which the concentration of the analyte of the bodily fluid typically changes. For instance when determining the concentration of blood glucose in the vicinity of a blood vessel the diffusion time of glucose in the respective tissue always has to be taken into account. Depending on the area or body part to which the spectroscopic analysis is applied, the diffusion time of the analyte may strongly vary. The diffusion time of glucose is governed by the so called glucose transporters, which are tissue specific membrane proteins that enable transport of glucose through cell membranes of cells forming the tissue surrounding e.g. blood capillaries.

As already described above, glucose can diffuse freely through the capillary walls into the interstitial fluid between the cells of bodily tissue. From Einstein's relation the average time that a glucose molecule needs to diffuse over a distance of 100 µm is estimated to be around 5 s, when assuming a diffusion coefficient of $1*10-9$ m$^2$/s as measured in water. Since glucose is presumably transported paracellular, i.e. not through the cells but around them, the transport distance may be considerably longer than the measured dimensions of the tissue. Further, a net transport of glucose through the tissue only occurs in the case of a concentration gradient. As an example, applying Fick's law and assuming a concentration difference of 1 mM and a diffusion distance of 100 µm, the glucose flux can be estimated to be about 6 molecules/s, if the capillary surface is around 1 µm$^2$.

According to Stryer L., Biochemistry 4$^{th}$ edition, W.H. Freeman and Company, New York 1995 there exists a variety of glucose transporters, denoted as GLUT that are particularly adapted for glucose transportation in various kinds of tissue. For instance, GLUT 1 provides glucose transportation for nearly all mammalian cells, erythrocytes, placenta, or fetal tissue. GLUT 2 is particularly relevant for glucose transportation in liver, kidney, intestine and pancreatic β-cell. GLUT 3 is provides glucose transportation in the brain and GLUT 4 serves to transport glucose in skeletal muscles, cardiac muscles, and in adipose (fat) tissue.

According to a further preferred embodiment of the invention, the capillary vessel comprises a blood vessel and the analyte is blood glucose. In this way the spectroscopic apparatus is particularly operable to determine blood glucose concentration of blood flowing through blood vessels of a person or an animal. Generally, the spectroscopic apparatus provides in vivo non-invasive blood glucose concentration making use of a spectroscopic analysis performed in tissue surrounding a capillary blood vessel.

According to a further preferred embodiment of the invention, the spectroscopic analysis unit is further adapted to determine the analyte concentration by making use of distance information between the capillary vessel and the volume. Making use of an appropriate calibration of the spectroscopic apparatus by determining the glucose concentration in the vicinity of a blood vessel, also the glucose concentration in the capillary vessel can be derived. Having knowledge of the glucose or analyte transport properties of the surrounding tissue and having knowledge of the distance between capillary vessel and the volume, determination of a glucose or analyte concentration within the volume is generally sufficient for a precise and reliable determination of the glucose concentration of the bodily fluid flowing inside the capillary vessel.

In another aspect the invention provides a method of determining a concentration of an analyte of a bodily fluid that is located in a first volume which is confined by a capillary vessel wall of a biological sample. The capillary vessel wall is at least semipermeable for the analyte and the method comprises determination of a position of the first volume and determination of a second volume with respect to the position of the first volume. The second volume does substantially not overlap with the first volume. Hence, first and second volumes are therefore separated by a predefined distance. After having specified the second volume, which is typically in close proximity to the first volume and therefore in close proximity to a capillary vessel, the inventive method provides application of excitation radiation into the second volume by means of a radiation source and a radiation guiding arrangement.

In response to impingement of excitation radiation in the second volume, various scattering processes of either elastic or inelastic type may occur, the latter of which typically features a wavelength shift being allowing to identify those molecules that are located inside the second volume. Detection of scattered radiation and in particular of inelastically scattered radiation emanating from the second volume allows to perform a spectral analysis for determining the concentration of a specific analyte.

In a preferred embodiment the inventive method further provides determining of at least a third volume that does substantially not overlap with the first volume. This at least third volume is determined with respect to the position and/or geometry and size of the first volume and/or with respect to the position and/or geometrical structure of the second volume. In an additional successive step the excitation radiation is then also directed into the at least third volume by means of the radiation guiding arrangement. Typically, the excitation radiation is focused into the at least third volume by means of a focusing arrangement of the radiation guiding arrangement. Accordingly, return radiation emanating from the third volume is detected and exploited for spectral analysis. In this embodiment spectroscopic investigation of the second and the at least third volume is typically performed successively. Further, the second and the at least third volumes may at least partially overlap.

In another aspect the invention provides a computer program product for a spectroscopic apparatus for determining a concentration of an analyte of a bodily fluid, which is located in a capillary vessel that is confined by a capillary vessel wall of a biological sample. The capillary vessel wall is at least semipermeable for the analyte, thus providing diffusion of an analyte of interest into the vicinity of the capillary vessel. The computer program product is operable by the spectroscopic apparatus and comprises computer program means for processing of an output of an imaging system for obtaining position information of the capillary vessel, for determining a volume by making use of the position information, wherein the volume is substantially not overlapping with the capillary vessel. The computer program means further provide control of a radiation guiding arrangement for directing excitation radiation into the volume. The program means are further adapted to process an output signal of a detector of the spectroscopic apparatus for spectral analysis of return radiation that is detectable by the detector.

Further, the computer program means of the computer program product provide determination of the concentration of the analyte by making use of the position information and the spectral analysis of the detected return radiation. The determined concentration of the analyte may either refer to the analyte concentration in the volume or an analyte concentration within the capillary vessel.

Figure 2:
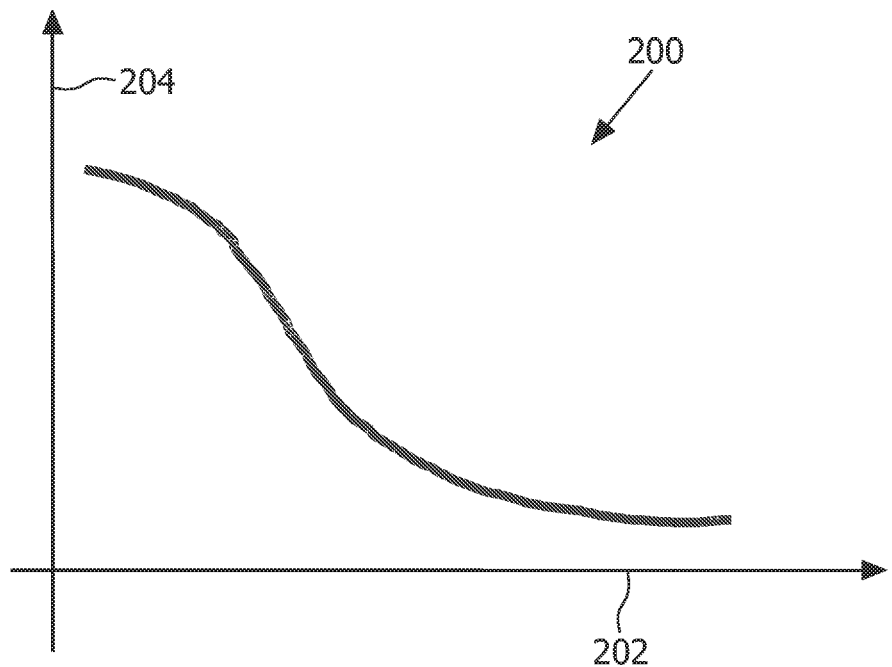
Figure 3:
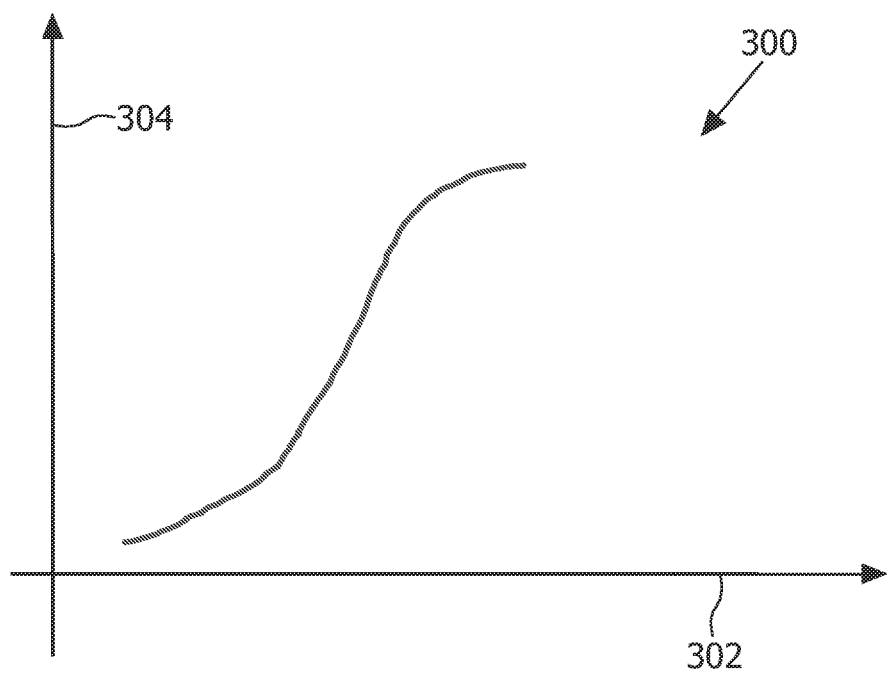
Figure 4:
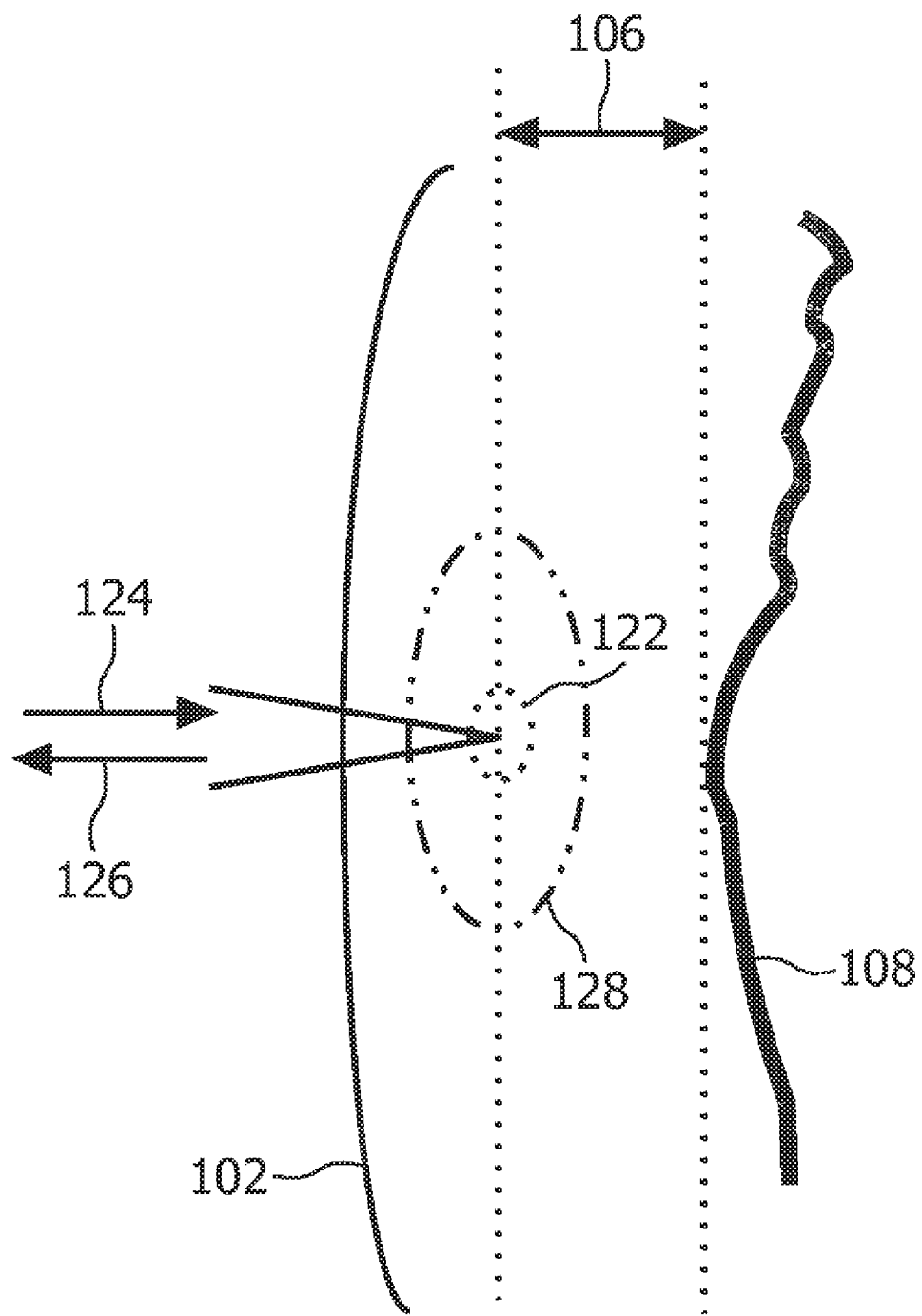
Figure 5:
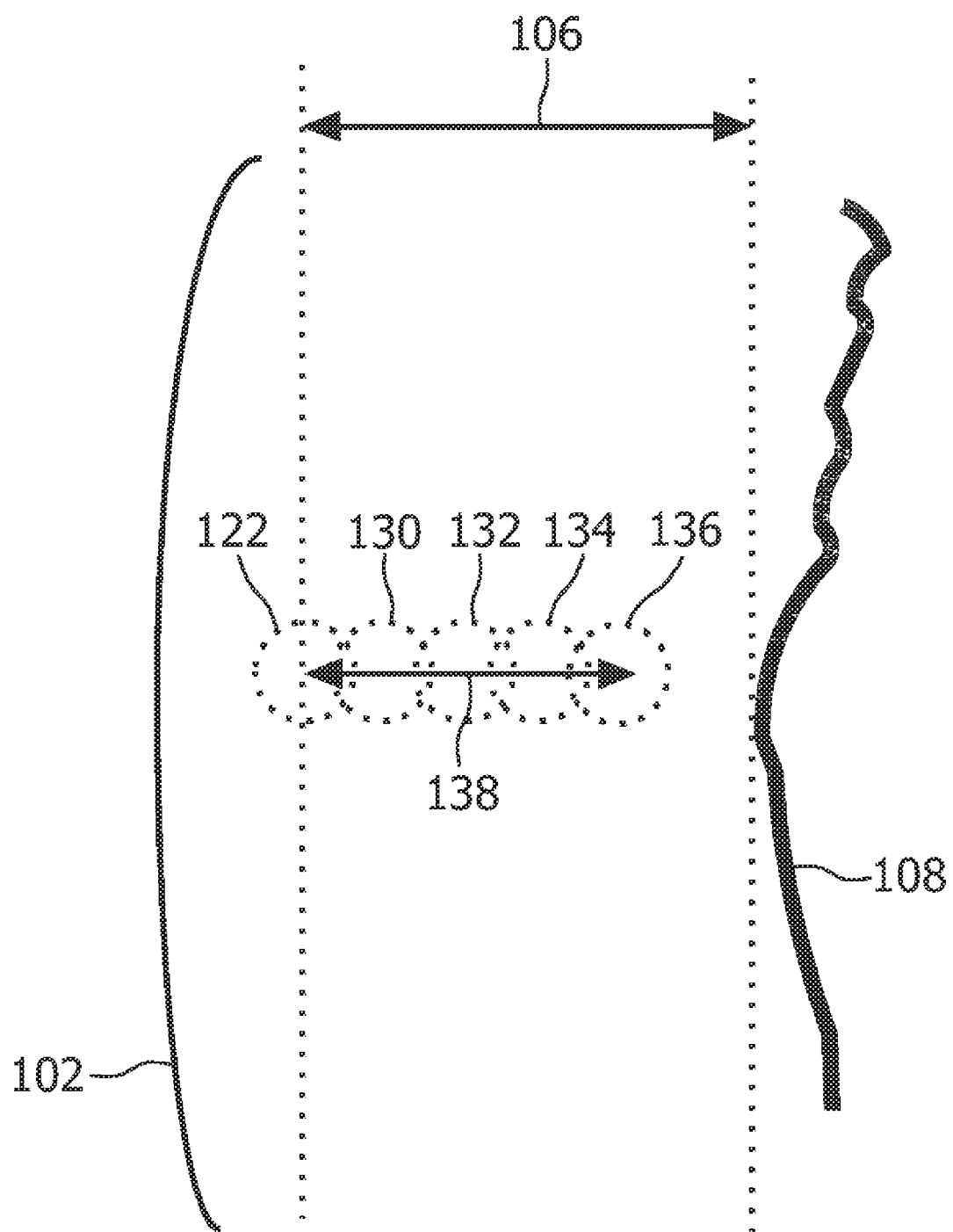
Figure 6:
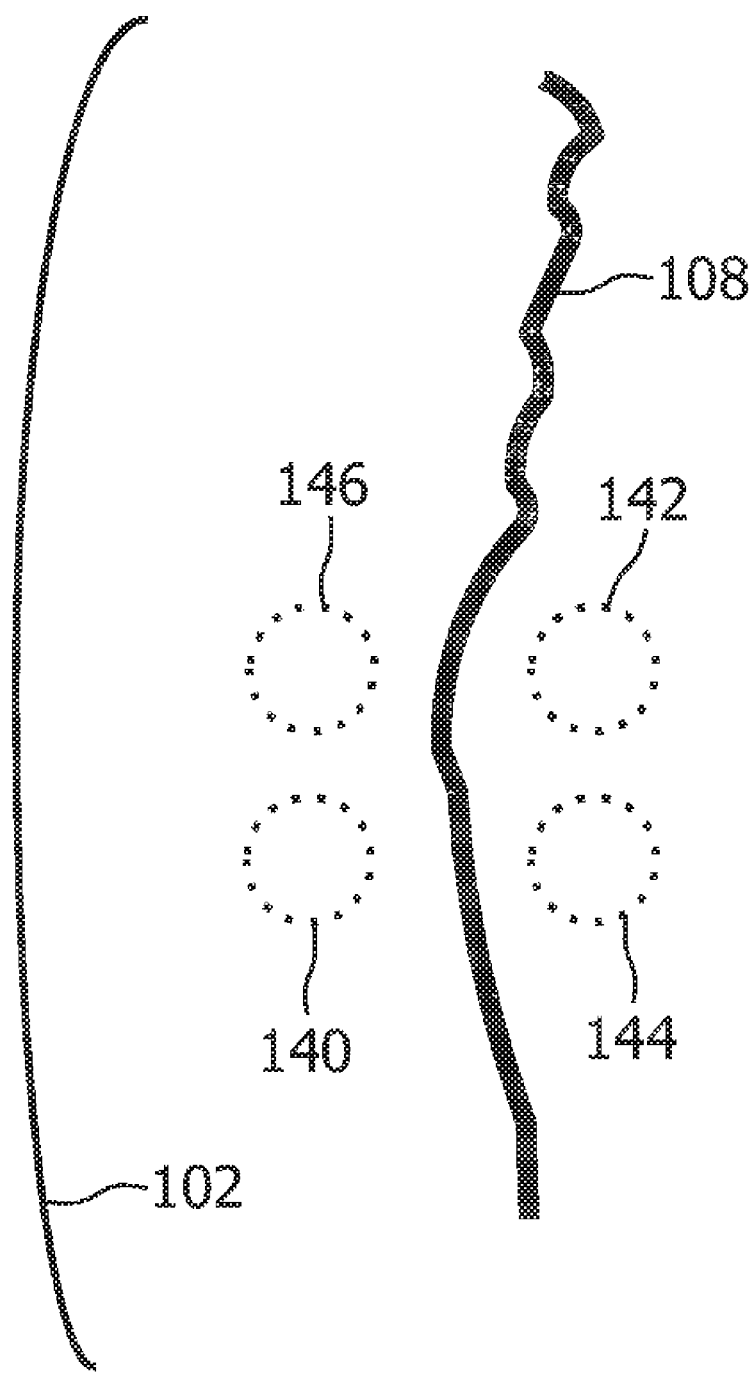
Figure 7:
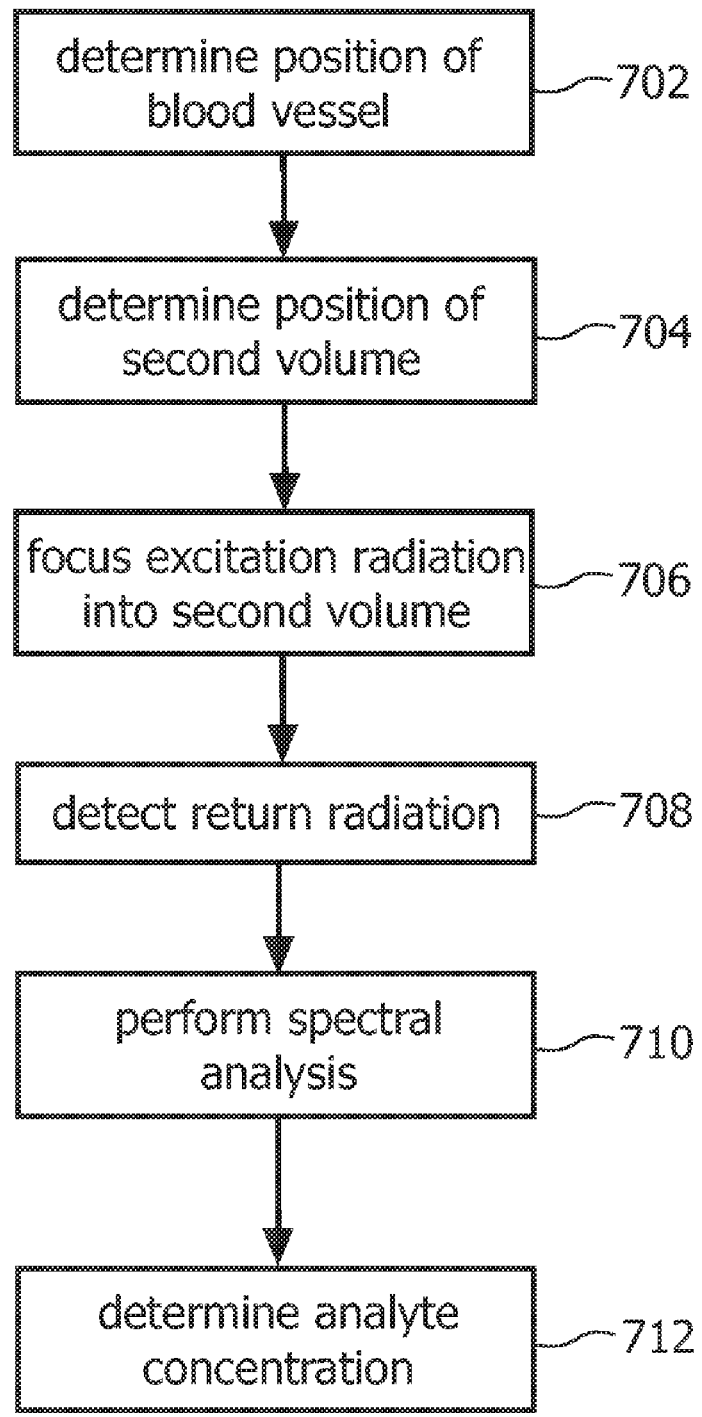

Further, it is to be noted that any reference signs in the claims are not to be construed as limiting the scope of the present invention In the following, preferred embodiments of the invention will be described in detail by making reference to the drawings in which:

FIG. 1 schematically shows a block diagram of the inventive spectroscopic apparatus, FIG. 2 depicts an analyte concentration level vs. distance from the capillary vessel, FIG. 3 depicts lag time of the analyte concentration vs. distance, FIG. 4 schematically shows volumes of different size, FIG. 5 schematically shows lateral displacement of the volume, FIG. 6 schematically shows four different volumes successively becoming subject to spectroscopic analysis, FIG. 7 shows a flowchart of the inventive method.

FIG. 1 shows a schematic block diagram of the spectroscopic apparatus and its major components. The spectroscopic apparatus 100 has a radiation source 118, a light coupling arrangement 110, a focusing lens 112, an imaging system 114, a spectroscopic analysis unit 116 and a control unit 120. In the illustrated embodiment, the spectroscopic apparatus 100 is applicable to skin tissue of e.g. a human patient. The tissue or body part of the human patient comprises a blood vessel 104 underneath of the surface of the skin 102. The blood vessel 104 features a blood vessel wall 108 that is highly permeable for the analyte that shall become subject to concentration determination, like e.g. blood glucose.

The shape and dimensions of the blood vessel 104 specify a first volume, whose location and structure is determined by means of the imaging system 114. Preferably, imaging as well as spectroscopic analysis is performed by making use of the common objective lens 112. Even though imaging as well as spectroscopic analysis may both make use of a common radiation source 118, also an additional light source for image acquisition might be implemented, e.g. operating in a different spectral range than the radiation source 118 which typically provides excitation radiation in the near infrared or infrared spectral range.

The spectroscopic apparatus 100 makes effective use of the fact, that e.g. blood glucose is capable of penetrating through the vessel wall 108 of a blood vessel 104. Therefore, in order to minimize scattering effects of red blood cells as well as to reduce an impact of interference of spectroscopic signals, the excitation radiation is preferably focused into an inspection volume 122, which is located at a predefined distance 106 with respect to the position of the blood vessel 104. Hence, the inventive spectroscopic apparatus makes effective use of biological transport processes, such as e.g. diffusion, therefore principally allowing to detect a blood glucose concentration not inside a blood vessel but in close proximity outside a blood vessel.

The distance 106 between the blood vessel 104 and the spectroscopic inspection volume 122 is governed by the permeability of the vessel wall 108 as well as by the underlying analyte transport properties of the tissue surrounding the blood vessel 104. Typically, with increasing distance 106, the concentration level of the analyte decreases. Therefore, the distance 106 shall not exceed a predefined maximum distance for which the analyte concentration gradient may drop below a minimum value.

The imaging system 114 of the spectroscopic apparatus 100 is adapted to acquire images of the area in the vicinity of the blood vessel 104 and might be provided with image processing means allowing to identify or to recognize the position, geometry and course of the blood vessel 104 underneath the surface of the skin 102. The imaging system can for instance be implemented by making use of e.g. Orthogonal Polarized Spectral Imaging (OPSI), Confocal Video Microscopy (CVM), Optical Coherence Tomography (OCT), Confocal Laser Scanning Microscopy (CLSM), Doppler based imaging, photoacoustic and ultrasound based imaging.

Based on the image acquisition performed by the imaging system 114 and subsequent image processing, the control unit 120 is adapted to autonomously determine the location and size of the inspection volume or excitation volume 122. Determination of the inspection or excitation volume 122 may further be performed with respect to parameters classifying the tissue surrounding the blood vessel 104. For instance, determination of the position and size of the inspection volume may be performed with respect to the blood glucose diffusion speed of the tissue and/or with respect to the tissue specific spatial blood glucose concentration gradient in the tissue. Alternatively, also the detection volume might be determined irrespectively of the size of the excitation or inspection volume, i.e. based on the image processing, the control unit may autonomously specify the size and/or location within the excitation volume from which emanating return radiation is detected for spectroscopic analysis.

Once the inspection volume 122 has been determined by the control unit 120, excitation radiation 124 provided by the radiation source 118 is focused into the inspection volume 122. In particular that portion of the return radiation 126 that has been subject to inelastic scattering in the inspection volume 122 and therefore provides a wavelength shift compared to the wavelength of the excitation radiation 124 can be effectively exploited for spectral analysis and principally allows to determine the concentration of a distinct analyte being located inside the inspection volume 122.

Generally, there exist various constellations of how to make use of inspection volume, excitation volume and detection volume. First, excitation and detection volume might entirely coincide and may be used to successively scan the inspection volume with a relatively small detection and excitation volume. Second, excitation and detection volume might be as large as the entire inspection volume and third, the excitation volume may completely coincide with the inspection volume whereas the relatively small detection volume is used to successively scan the area of the inspection volume.

Separation of elastically and inelastically scattered return radiation 126 is effectively performed by the light coupling arrangement 102, which typically comprises various beam splitters and dichroic elements providing a wavelength specific deflection of the spectral components of the return radiation 126.

If appropriately calibrated, the spectroscopic apparatus 100 not only provides concentration determination of the analyte inside the inspection volume 122 but also provides analyte concentration determination inside the blood vessel 104 by making use of a correlation between analyte concentration levels inside the inspection volume 122 and inside the blood vessel 104. Having knowledge of e.g. a correlation of the blood glucose concentration level inside and outside the blood vessel 104 and having further knowledge of a typical spatial blood glucose concentration gradient in the surrounding tissue, by determining the blood glucose concentration inside the inspection volume 122 and by determining the distance 106 between inspection volume 122 and blood vessel 104, also the blood glucose concentration level inside the blood vessel 104 can be precisely derived.

FIG. 2 schematically shows a diagram 200 exemplary illustrating blood glucose concentration 204 versus distance 202 from a blood vessel 104. It can clearly be seen that with increasing distance from the blood vessel, the blood glucose concentration decreases monotonously. By means of a calibration procedure such spatial blood glucose concentration gradients can be recorded and stored and may serve as a reliable means for correlating a blood glucose concentration measure outside a capillary vessel to a blood glucose concentration inside the capillary vessel. Since the blood glucose concentration level constantly drops for increasing distance from the blood capillary, it is advantageous to specify a maximum distance 106 between the inspection volume 122 and the capillary vessel 104.

FIG. 3 schematically illustrates a graph 300 displaying a lag time of the analyte concentration 304 versus distance 302 from the blood vessel 104. The lag time specifies a time interval after which a change of the analyte concentration in the blood vessel 104 can be measured in the inspection volume 122 that is located at a given distance 302. The lag time increases constantly with increasing distance and is further governed by the underlying biological transport mechanism of the surrounding tissue. For instance, the lag time reflects the diffusion speed of the analyte in the tissue surrounding the blood vessel. It therefore represents a temporal delay between analyte concentration changes that occur in the blood vessel 104 and in the inspection volume 122.

Since the lag time increases with increasing distance from the blood vessel, it is advantageous to specify an upper limit for the distance 106 in order to guarantee that a change in the analyte concentration within the blood vessel can be detected by the inventive method within a predetermined time interval. This aspect is extremely relevant in emergency situations, where the blood glucose concentration may drop below a critical value thus causing a clinical shock state of the patient.

FIG. 4 schematically illustrates various inspection volumes 122 and 128 to which excitation radiation can be applied. For example, inspection volume 122 represents the focal spot size of the excitation radiation 124 covering an area which is of a similar size than the diameter of the blood vessel 108. This rather focused spot provides a rather large radiation density in the inspection area 122 leading to a corresponding large intensity of the scattered radiation 126. However, scattered radiation obtained from rather small focal spots is also quite sensitive to variations of the morphology or biological structure of the irradiated tissue. Hence, the spectrum of scattered radiation obtained from radiation focused inside a cell may drastically vary from the spectrum that is obtained when the focal spot is directed into interstitial fluid between the cells.

Therefore, the light guiding arrangement and its focusing arrangement of the spectroscopic apparatus 100 provide variation of the focal spot size of the excitation radiation inside the second volume. Hence, the focal spot described by the inspection volume 122 can for instance be enlarged to the inspection volume 128. In this case the radiation intensity typically decreases but scattering processes occur in a variety of different biological structures, thus leading to a spatial averaging of the spectrum of the return radiation 126.

FIG. 5 schematically shows a lateral displacement of the second volume underneath of the surface of the skin Here, the various positions of the inspection volume 122 are indicated by positions 130, 132, 134 and 136. As can be seen, the inspection volume 122 has been displaced along a horizontal inspection path 138 as indicated by the arrow. In this way the concentration of the analyte can be determined at various different distances from the capillary vessel 104. Typically, the inspection volume 122, hence the focal spot of the excitation radiation, is moved along the inspection path 138 during detection of return radiation from the respective focus spots. In this way the inventive method even allows to determine a spatial analyte concentration gradient, which in turn can be exploited as an indicator for diseases, such as diabetics. For instance, blood vessels of diabetic patients typically feature a different permeability with respect to blood glucose compared to blood vessels of healthy persons. In this way by measuring a spatial glucose concentration gradient an indication of a disease might be directly obtained.

The inspection path 138 does by no means have to be substantially perpendicular to the elongation of the blood vessel 108. For instance, the inspection path 138 may also specify numerous inspection volumes, each of which featuring the same distance to the blood vessel 108. As an example the various inspection volumes 130, . . . , 136 may be arranged in a vertical direction mimicking the course of the blood vessel 108. In this constellation, the successively obtained spectra can be mutually combined for an averaging procedure allowing for effective elimination of measurement artefacts.

FIG. 6 shows an alternative embodiment, where various inspection volumes 140, 142, 144 and 146 are arranged in a rectangular like way in close vicinity to the blood vessel 108. In this constellation each of the inspection volumes 140, . . . , 146 essentially features a comparable distance to the blood vessel. Therefore, spectra that may be obtained from these inspection volumes should all represent a similar analyte concentration level. Hence, combining of the spectra that correspond to the indicated inspection volumes provides an effective means of averaging and error elimination.

FIG. 7 illustrates a flowchart of performing the inventive method of determining of the analyte concentration. In a first step 702, the position and/or geometry as well as the course of a blood vessel is determined by making use of the imaging system. Based on the obtained image of the blood vessel and successive image processing, in a following step 704 the position of the second volume, i.e. the inspection volume is determined. Determination of the position and/or size of the second volume is typically performed with respect to the position of the blood vessel as well as with respect to the transport properties of the tissue surrounding the blood vessel.

After determination of the inspection volume, in a successive step 706 spectroscopic excitation radiation generated by the radiation source is focused into the determined second volume, which typically leads to a variety of elastic and inelastic scattering processes. In a further, not illustrated step, the detection volume of the spectroscopic apparatus may be adapted and adjusted with respect to the size and/or position of the excitation or inspection volume.

During irradiation of excitation radiation into the second volume, in the following step 708 scattered return radiation is detected by means of a detector whose output is processed and analyzed in step 710. Here, a spectral analysis of the return radiation is performed by making use of a spectrometer. Based on the analyzed spectrum in a final step 712, the concentration of the analyte can be determined. Additionally, by making use of a distance parameter between the second volume and the position of the blood vessel as well as by making use of classified diffusion properties of the surrounding tissue, also the analyte concentration within the blood vessel can be precisely derived.

In essence, the invention provides non-invasive determination of blood glucose concentration by making use of spectral analysis of tissue in close vicinity of a blood vessel. Since the spectroscopic inspection volume does substantially not overlap with the blood vessel, a disadvantageous signal degradation due to scattering from red blood cells as well as temporal variations of an obtained spectroscopic signal that are due to the blood flow can be effectively reduced to a minimum. Also, effects of interference of spectroscopic signals arising from various non-relevant analytes of the blood can be effectively eliminated.

LIST OF REFERENCE NUMERALS 100 spectroscopic apparatus
102 skin
104 blood
106 distance
108 vessel wall
110 light coupling arrangement
112 focusing lens
114 imaging system
116 spectroscopic analysis unit
118 radiation source
120 control unit
122 inspection volume
124 excitation radiation
126 return radiation
128 inspection volume
130 inspection volume
132 inspection volume
134 inspection volume
136 inspection volume
138 inspection path
140 inspection volume
142 inspection volume
144 inspection volume
146 inspection volume
200 diagram
202 distance
204 analyte concentration
300 diagram
302 distance
304 analyte concentration

The invention claimed is:

1. A spectroscopic apparatus for determining a concentration of an analyte of a bodily fluid located in a capillary vessel the spectroscopic apparatus comprising:
    an imaging system for determining a position of the capillary vessel;
    a radiation source for generating excitation radiation;
    a radiation guiding arrangement for directing excitation radiation into a volume non-overlapping with the capillary vessel;
    a radiation detector for detecting return radiation emanating from the volume; and
    a spectroscopic analysis unit for determining the analyte concentration by spectrally analyzing the detected return radiation.

2. The spectroscopic apparatus according to claim 1, further comprising a control unit configured
    to determine the position of the volume with respect to the position of the capillary vessel, and in response
    to receive an input from the imaging system.

3. The spectroscopic apparatus according to claim 1, wherein the radiation guiding arrangement comprises a focusing arrangement for focusing the excitation radiation into the volume, the focusing arrangement varying the focal spot size of the excitation radiation in the volume.

4. The spectroscopic apparatus according to claim 3, wherein the volume is movable with respect to the position of the capillary vessel during detection of return radiation.

5. The spectroscopic apparatus according to claim 1, wherein the capillary vessel comprises a blood vessel and the analyte is blood glucose.

6. The spectroscopic apparatus according to claim 1, wherein the spectroscopic analysis determines the analyte concentration using the distance information between the capillary vessel and the volume.

7. The spectroscopic apparatus according to claim 2, wherein the control unit is configured to control the radiation guiding arrangement for successively directing excitation radiation into volumes featuring varying of the distance to the capillary vessel for determination of a gradient of the analyte concentration.

8. A method of determining a concentration of an analyte of a bodily fluid being located in a first volume confined by a capillary vessel wall being at least semipermeable for the analyte, the method comprising acts of:
  determining a position of the first volume;
  determining a second volume with respect to the position of the first volume, the second volume being non-overlapping with the first volume and the capillary vessel;
  directing excitation radiation into the second volume by means of a radiation guiding arrangement; and
  detecting return radiation emanating from the second volume and performing a spectral analysis of the detected return radiation for determining the concentration of the analyte.

9. The method according to claim 8, further comprising acts of:
  determining at least a third volume in the proximity of the first volume with respect to the position of the first volume and/or with respect to the second volume;
  directing excitation radiation into the at least third volume by means of the radiation guiding arrangement;
  detecting a second return radiation emanating from the third volume; and
  determining the concentration of the analyte by making use of the spectral analysis of the return radiation and the spectral analysis of the second return radiation.

10. The method according to claim 9, wherein the second and third volumes are different in size and/or wherein the second and third volumes become subject to spectral analysis successively.

11. The method according to claim 10, further comprising acts of:
  determining a concentration gradient of the analyte; and
  comparing the determined concentration gradient with reference gradients for detection of a disease.

12. A non-transitory computer program product operable by a spectroscopic apparatus for determining a concentration of analyte of a bodily fluid located in a capillary vessel, when executed by the spectroscopic apparatus the computer program performs acts of:
  processing an output of an imaging system for obtaining position information of the capillary vessel;
  determining a volume by making use of the position information, the volume being non-overlapping with the capillary vessel;
  controlling a radiation guiding arrangement for directing excitation radiation into the volume;
  processing an output signal of a detector of the spectroscopic apparatus for spectral analysis of return radiation being detectable by the detector; and
  determining the concentration of the analyte by making use of the position information and the spectral analysis of the detected return radiation.

* * * * *